United States Patent [19]
Annoura et al.

[11] Patent Number: 5,843,988
[45] Date of Patent: Dec. 1, 1998

[54] CYCLOPROPACHROMENCARBOXYLIC ACID DERIVATIVES

[75] Inventors: Hirokazu Annoura, Kyoto; Atsuko Fukunaga, Kanagawa-ken; Toshio Tatsuoka, Hyogo-ken; Yoshiko Horikawa, Nara-ken, all of Japan

[73] Assignee: Suntory Limited, Japan

[21] Appl. No.: 817,389

[22] PCT Filed: Oct. 20, 1995

[86] PCT No.: PCT/JP95/02163

§ 371 Date: Apr. 18, 1997

§ 102(e) Date: Apr. 18, 1997

[87] PCT Pub. No.: WO96/12715

PCT Pub. Date: May 2, 1996

[30] Foreign Application Priority Data

Sep. 1, 1995 [JP] Japan .................................. 7-225365
Oct. 21, 1997 [JP] Japan .................................. 6-256468

[51] Int. Cl.$^6$ .................. A61K 31/41; C07D 311/20; C07D 311/78

[52] U.S. Cl. .................. 514/454; 514/455; 549/359; 549/458

[58] Field of Search .................... 549/458, 359; 514/454

[56] References Cited

U.S. PATENT DOCUMENTS 5,155,129 10/1992 Tatsuoka et al. .................. 514/454

FOREIGN PATENT DOCUMENTS 0 460 359 A2 12/1991 European Pat. Off. .

OTHER PUBLICATIONS

Chemical Abstracts 125:33436z (1996) Annoura et al.
Chemical Abstracts, vol. 125(3),abst.No.33,436z,pub.Jul. 15, 1996.
Chemical Abstracts,vol.125,(9),abst.No.114,483q,pub.Aug. 26, 1996.

*Primary Examiner*—Alan L. Rotman
*Attorney, Agent, or Firm*—Nixon & Vanderhye

[57] ABSTRACT

The present invention provides novel cyclopropachromen-carboxylic acid derivatives having an antagonistic activity against metabotropic glutamate receptors and its pharmaceutically acceptable salts. Cyclopropachromen-carboxylic acid derivatives and its pharmaceutically acceptable salts represented by the following general formula (1):

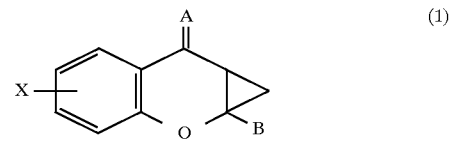

(1)

[wherein A denotes an oxygen atom, hydroxyimino group, an alkyloxyimino group having 1 to 5 carbon atoms, or the group $=N-O-(CH_2)_n-NR^1R^2$ (where n represents an integer of 2 to 8, and each of $R^1$ and $R^2$ independently represents a hydrogen atom or alkyl group having 1 to 5 carbon atoms, respectively); B denotes the group $-COOR^3$ (where $R^3$ represents a hydrogen atom or alkyl group having 1 to 5 carbon atoms) or the group $-CONR^4R^5$ (where $R^4$ and $R^5$ independently represent a hydrogen atom, alkyl group having 1 to 5 carbon atoms, alkenyl group having 2 to 5 carbon atoms and an aminoalkyl group.

5 Claims, No Drawings

CYCLOPROPACHROMENCARBOXYLIC ACID DERIVATIVES

CROSS REFERENCE

This Application is a 371 of PCT/JP95/02163 filed Oct. 20, 1995.

BACKGROUND OF THE INVENTION

The present invention relates to novel cyclopropachromencarboxylic acid derivatives and pharmaceutically acceptable salts. More specifically, the present invention relates to novel cyclopropachromen-carboxylic acid derivatives and pharmaceutically acceptable salts, which are endowed with antagonistic activity against metabotropic glutamate receptors, and which are effective for ameliorating and treating symptoms of ischemic disorders in the brain such as sequelae of cerebral infarction, sequelae of intracerebral hemorrhage, sequelae of cerebral arteriosclerosis, and so on and symptoms of organic brain disorders such as senile dementia, sequelae of head trauma, sequelae of surgical brain operation, Alzheimer's disease, Parkinson's disease, and so on.

It is generally recognized that the pathogenesis of progressive, delayed death of nerve cells followed by brain injury associated with head trauma or cerebrovascular disorders (e.g. intracerebral hemorrhage, transient ischemic attack, cerebral infarction) involves abnormal activation of glutamate receptors due to excessive release of glutamic acid, i.e. an excitatory neurotransmitter in vivo[D. T. Monaghan et al.: Annu. Rev. Pharmacol. Toxicol., 29, 365 (1989); B. Meldrum et al.: Trends Pharmacol. Sci., 11,379 (1990)]. Glutamate receptors are classified into two major types: ionotropic receptors (iGluR), which directly gate ion channels, and metabotropic receptors (mGluR) which are linked to an intracellular signaling system via G proteins [S. Nakanishi, Science, 258, 597(1992)], and their antagonists are currently under investigation for developing drugs for preventing or inhibiting the death of nerve cells. However, most of such antagonists are those against iGluR [J. C. Watkins et al.:Trends Pharmacol. Sci., 11, 25 (1990); D. Lodge et al.: ibid. 11, 81(1990)]. With regard to [D. Bleakman et al. : Mol. Pharmacol., 42. 192(1992); J. W. McDonald et al. :J. Neurosci, 13, 4445(1993)] which recently have been suggested to involve the death of nerve cells, only L-AP3 [D. Schoepp et al.: Trends Pharmacol. Sci., 14, 13 (1993)] and phenyglycine derivatives [Y. Hayashi et al.: J. Neurosci., 14, 3370 (1994)] have been reported.

SUMMARY OF THE INVENTION

With the aforementioned background, it is an objective of the present invention to provide novel compounds, which have mGluR antagonistic activity, and which are useful in ameliorating and treating functional and organic disorders in the brain.

DETAILED DESCRIPTION OF THE INVENTION

The present inventors found that cyclopropacromen derivatives protect the brain in a hypoxic state under reduced pressure, and filed a patent application for the resulting invention (please refer to Japanese Patent Application Laid-Open (KOKAI) No.235180/92. Further, the present inventors took particular note of mGluR1, which is an mGluR subtype coupled with hydrolysis of inositol phospholipids [M. Masu et al.: Nature, 349, 760 (1991)], and synthesized a series of compounds for screening them in view of an antagonistic activity against intracellular calcium ion elevation, which is induced by glutamic acid, using Chinese hamster ovary (CHO) cells in which recombinant gene for rat mGluR1 is transfected [S. Nakanishi et al.: Neuron., 8, 757 (1992)]. The study demonstrated that cyclopropachromencarboxylic acid derivatives have antagonistic activity against mGluR1 and that the derivatives have improved stability as compared with known cyclopropachromen derivatives, and therefore, the present invention has been completed.

The present invention provides, as an mGluR1 antagonist, a cyclopropachromencarboxylic acid derivative and its pharmaceutically acceptable salts represented by the following general formula (1)

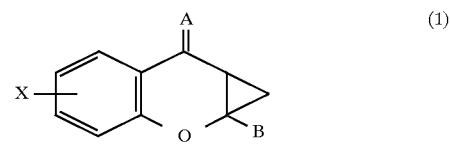

(1)

[wherein A denotes an oxygen atom, hydroxyimino group, an alkyloxyimino group having 1 to 5 carbon atoms, or the group $=N-O-(CH_2)_n-NR^1R^2$ (where n represents an integer of 2 to 8, and each of $R^1$ and $R^2$ independently represents a hydrogen atom or alkyl group having 1 to 5 carbon atoms, respectively);

B denotes the group $-COOR^3$ (where $R^3$ represents a hydrogen atom or alkyl group having 1 to 5 carbon atoms) or the group $-CONR^4R^5$ (where $R^4$ and $R^5$ independently represent a hydrogen atom, alkyl group having 1 to 5 carbon atoms, alkenyl group having 1 to 5 carbon atoms, aminoalkyl group wherein N may be substituted, phenyl group which may be substituted with a halogen atom or hydroxyl group which in turn may be substituted, 2-pyridyl group, or aralkyl group having 7 to 10 carbon atoms, or, $R^4$ and $R^5$ taken together with the nitrogen atom to which they are attached form a nitrogen-containing heterocyclic ring-system which may be substituted); and X is a halogen atom or the group $-OR^6$ (where $R^6$ represents a hydrogen atom, alkyl group having 1 to 5 carbon atoms, an alkenyl group having 3 to 6 carbon atoms, or an aralkyl group having 7 to 10 carbon atoms)].

In general formula (1), the alkyloxyimino group having 1 to 5 carbon atoms represented by A is exemplified by methoxyimino group, ethoxyimino group, straight-chain or branched propaoxyimino group (e.g. 3-methylaminopropyl-oxyimino group), straight-chain or branched butoxyimino group and straight-chain or branched pentoxyimino group. In the group $=N-O-(CH_2)n-NR^1R^2$ represented by A, n denotes an integer of 2 to 8, preferably an integer of 2 to 4, and more preferably 3. Examples of the alkyl group having 1 to 5 carbon atoms represented by $R^1$ and $R^2$ include methyl group, ethyl group, straight-chain or branched propyl group, straight-chain or branched butyl group and straight-chain or branched pentyl group, and methyl group or ethyl group is preferred among them.

The alkyl group having 1 to 5 carbon atoms represented by $R^3$ in the group $-COOR^3$ represented by B in general formula (1) is exemplified by a methyl group, ethyl group, straight-chain or branched propyl group, straight-chain or branched butyl group and straight-chain or branched pentyl group, among which a methyl group, ethyl group or isobutyl group is preferable.

As examples of the alkyl group having 1 to 5 carbon atoms represented independently by $R^4$ and $R^5$ in the group —COONR$^4$R$^5$ represented by B in general formula (1), a methyl group, ethyl group, straight-chain or branched propyl group, straight-chain or branched butyl group and straight-chain or branched pentyl group can be listed, among which a methyl group or ethyl group is preferable. Furthermore, this alkyl group may be replaced by an alkenyl group, that is a double bond may be introduced.

The aminoalkyl group represented independently by $R^4$ and $R^5$ refers to an alkyl group having 1 to 5 carbon atoms wherein an amino group substitutes at the terminal methyl moiety of a methyl group, ethyl group, straight-chain or branched propyl group, straight-chain or branched butyl group or straight-chain or branched pentyl group, or further refers to a nitrogen-containing heterocycle, which is formed by cyclization of the amino group with the alkyl moiety, such as pyrrolidinyl group or piperidyl group. The nitrogen atom in the amino group or the nitrogen-containing heterocycle may be substituted with a group such as an alkyl group having 1 to 5 carbon atoms or benzothiazolyl group, or a protecting group such as t-butoxycarbonyl group.

The substituent of the phenyl group represented independently by $R^4$ and $R^5$ is exemplified by a halogen atom such as a fluorine atom, a chlorine atom, a bromine atom or an iodine atom, and preferably a fluorine atom or a chlorine atom. The phenyl group may be substituted with one or a plurality of hydroxyl groups, and the hydroxyl group thereof may be substituted with alkyl group having 1 to 5 carbon atoms or an ether-type protecting group such as methoxymethyl (MOM) group, methoxyethoxymethyl group (MEM) group and 2-(trimethylsilyl)ethoxymethyl (SEM) group. Furthermore, the aralkyl group having 7 to 10 carbon atoms represented independently by $R^4$ and $R^5$ includes a benzyl group, as a typical example.

As examples of the nitrogen-containing heterocyclic group represented by NR$^4$R$^5$ in its combined form, a piperidino group, piperazinyl group, morpholino group or thiomorpholino group may be mentioned. The 4-position of these nitrogen-containing heterocyclic groups may be substituted. The substituents include an aryl group such as phenyl group, benzothiazolyl group, benzooxyazolyl group, pyridyl group and pyrimidinyl group; an aralkyl group such as benzyl group which may be substituted with a phenyl group; and an amino group which may be substituted with an aryl group such as a phenyl group, benzothiazolyl group, benzoxyazolyl group, pyridyl group and pyrimidyl group. Further, these substituents may be substituted with a halogen atom.

The halogen atom represented by X in general formula (1) can be exemplified by a fluorine atom, a chlorine atom, a bromine atom and an iodine atom, preferably a fluorine atom and a chlorine atom.

For the alkyl group having 1 to 5 carbon atoms represented by $R^6$ in the group —OR$^6$, methyl group, ethyl group, straight-chain or branched propyl group, straight-chain or branched butyl group and straight-chain or branched pentyl group can be mentioned as examples, preferably methyl group and ethyl group. The alkenyl group having 3 to 6 carbon atoms represented by $R^6$ is exemplified by 2-propenyl group, and the aralkyl group having 7 to 10 carbons represented by $R^6$ is exemplified by a benzyl group and p-methoxybenzyl group. Further, $R^6$ may be substituted with an ether-type protecting group such as methoxymethyl (MOM) group, methoxyethoxymethyl group (MEM) group and 2-(trimethylsilyl)ethoxymethyl (SEM) group.

A preferred embodiment of the present invention includes a cyclopropachromencarboxylic acid derivative having the following general formula (2a) and (2b),

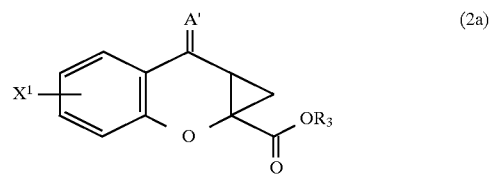

(2a)

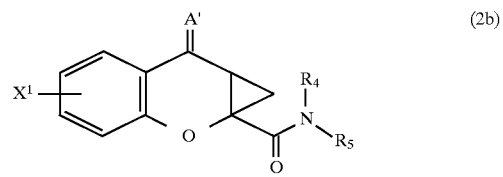

(2b)

[wherein, in the formula, A' represents an oxygen atom or hydroxyimino group;

$R^3$, $R^4$ and $R^5$ represents the aforementioned groups; and $X^1$ represents a hydrogen atom, a hydroxy group or 2-propenyloxy group.] The preferred embodiment provides particularly favorable compounds in view of activity, toxicity, and stability.

Among the compounds represented by general formula (1) of the present invention those which have an amino group in a side chain, may form, if desired, an addition salt with a pharmaceutically acceptable acid. Such an acid-addition salt is also included within the scope of the present invention. The acid-addition salt includes, for example, salts with an inorganic acid such as hydrochloric acid, hydrobromic acid, sulfuric acid, nitric acid and phosphoric acid, and so on; and salts with an organic acid such as acetic acid, oxalic acid, succinic acid, fumaric acid, tartaric acid, citric acid, maleic acid, benzoic acid and so on.

The compound represented by general formula (1) includes a compound having isomers, and the present invention includes all of such isomers. For example, the compound of general formula (1) has two optical isomers with respect to the cyclopropane ring moiety. When A represents hydroxyimino group, alkyloxyimino group having 1 to 5 carbon atoms or the group =N—O—(CH$_2$)$_n$—NR$^1$R$^2$ (wherein R$^1$, R$^2$, and n have the aforementioned meaning.), the compounds have two geometric isomers, i.e. the (E) isomer and the (Z) isomer with respect to the oxime moiety. The compound according to the present invention includes all of the isomers based on these combinations and a mixture thereof.

The compound according to the present invention may be synthesized, for example, as follows. Either the known compound or 4-oxo-4H-1-benzopyran-2-carboxylic acid derivative synthesized by the known method [G. P. Ellis et al.: J. Chem. Soc. (c), 2230 (1970)] is esterified or amidated in the standard manner. The obtained ester or amide compound is then treated with 1 to 10 equivalents of trimethylsulfoxonium iodide in a solvent not participating in the reaction such as dimethylsulfoxide, dimethylformamide, tetrahydrofuran, dioxane, benzene, toluene and the like in the presence of 1 to 10 equivalents of alkali metal base such as sodium, potassium, sodium hydride, potassium hydride, sodium amide, sodium ethoxide, potassium t-butoxide, sodium hydroxide, potassium hydroxide, and the like at −20° C. to 100° C., preferably at room temperature to 60° C., to obtain the cyclopropachromencarboxylic acid represented by general formula (1a)

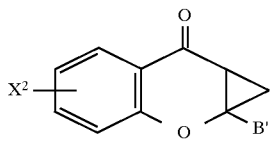
(1a)

[where B' represents the group —COOR⁶ (where R⁶ denotes an alkyl group having 1 to 5 carbon atoms) or the group —CONR⁴R⁵ (where R⁴ and R⁵ independently denote a hydrogen atom, alkyl group having 1 to 5 carbon atoms, an alkenyl group having 2 to 5 carbon atoms, an aminoalkyl group of which N may be substituted, a phenyl group which may be substituted with a halogen atom or with a hydroxyl group which in turn may be substituted, a 2-pyridyl group, or an aralkyl group having 7 to 10 carbon atoms, or, toghther with the nitrogen atom they are attached, a nitrogen-containing heterocyclic group which may be substituted), and X² denotes a halogen atom or the group —OR⁶ (where R⁶ represents alkyl group having 1 to 5 carbon atoms, an alkenyl group having 3 to 6 carbon atoms, an aralkyl group having 7 to 10 carbon atoms, methoxymethyl group, methoxyethoxymethyl group or 2-(trimethylsilyl)-ethoxymethyl group)].

The compound (1a) thus obtained can be converted into the oxime compound represented by general formula (1b) (wherein B' and X² denote the same groups as described above)

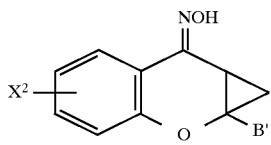
(1b)

by the reaction with hydroxyamine or its acid-addition salt in a solvent not participating in the reaction such as pyridine, water, alcohol or a water/alcohol mixture in the presence of a base such as pyridine, sodium hydroxide, potassium hydroxide, sodium hydrogen carbonate, potassium hydrogen carbonate, sodium carbonate or potassium carbonate. By allowing the obtained oxime compound (1b) to react with a halogenated alkyl having 1 to 5 carbon atoms in a solvent not participating in the reaction such as ether, tetrahydrofuran, dioxane, benzene, toluene, xylene, dimethylformamide, dimethylsulfoxide or alcohol in the presence of an alkali metal base such as sodium, potassium, sodium hydride, potassium hydride, sodium amide, sodium ethoxide, potassium t-butoxide, sodium hydroxide or potassium hydroxide for 1 to 24 hours at −20° C. to 120° C., preferably 0 to 80° C., the alkyloxime compound represented by general formula (1c) (wherein R refers to alkyl group having 1 to 5 carbon atoms, and B' and X² denote the same groups as the above described) is obtained.

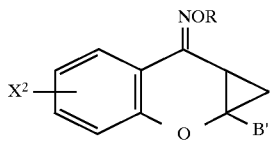
(1c)

The alkyloxime compound represented by general formula (1c) can also be obtained by oxime formation of the carbonyl compound (1a) in the same manner as above using O-alkylhydroxyamine. By allowing the oxime compound (1b) to react with the compound represented by general formula

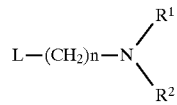
(3)

(wherein n denotes an integer from 2 to 8, R¹ and R² represent independently a hydrogen atom and alkyl group having 1 to 5 carbon atoms, and L denotes a halogen atom, tosyloxy group or methanesulfonyloxy group) in a solvent not participating in the reaction such as ether, tetrahydrofuran, dioxane, benzene, toluene, xylene, dimethylformamide, dimethylsulfoxide or alcohol in the presence of an alkali metal base such as sodium, potassium, sodium hydride, potassium hydride, sodium amide, sodium ethoxide, potassium t-butoxide, sodium hydroxide or potassium hydroxide for 1 to 24 hours at −20° C. to 120° C., preferably 0 to 80° C., the compound represented by general formula (1d) (wherein B', X², n, R¹ and R⁵ denote the same as defined above) is obtained.

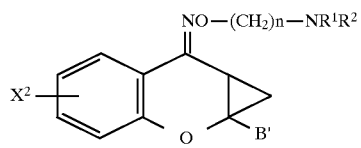
(1d)

By deallylation of any of the compounds (1a) to (1d) in which R⁶ of the group —OR⁶ represented by X² is 2-propenyl group according to the known method [A. B. Smith et al.: J. Am. Chem. Soc., 114, 9343 (1992)] in the presence of a catalytic amount of rhodium triphenylphosphine chloride complex, by hydrogenation of any of the compounds (1a) to (1d) in which R⁶ of the group —OR⁶ represented by X² is benzyl group or p-methoxybenzyl group in a solvent such as methanol, ethanol or isopropyl alcohol in the presence of a catalytic amount of Pd-C, or by treating any of the compounds (1a) to (1d) in which R⁶ of the group —OR⁶ represented by X² is methoxymethyl group, methoxyethoxymethyl group, or 2-(trimethylsilyl)ethoxymethyl group with an acid such as acetic acid, trifluoroacetic acid, hydrochloric acid or sulfuric acid, a compound represented by formula (1) where R⁶ of the group —OR⁶ represented by X denotes a hydrogen atom can be obtained. Further, a compound represented by formula (1) where R³ of the group —COOR³ represented by B is a hydrogen atom can be obtained by hydrolysis of any of the compounds represented by (1a) to (1d) by the known method.

Each isomer of the compound represented by general formula (1) can be separated by recrystallization, column chromatography, thin layer chromatography, high performance liquid chromatography, or the similar methods using optically active reagents.

The compounds represented by general formula (1) of the present invention have low toxicity and may be used alone or, if desired, prepared in combination with conventional pharmaceutically acceptable carriers to provide a pharmaceutical product for ameliorating and treating symptoms arising from various brain disorders. For example, the active ingredient may be prepared, alone or in combination with conventional vehicles into appropriate dosage forms such as capsules, tablets or injections and administered orally or parenterally. A capsule, for example, is prepared by the steps of admixing a bulk powder of the inventive compound with a vehicle such as lactose, starch, or a derivative thereof, or a cellulose derivative; and filling the mixture in gelatin capsules. A tablet is prepared by the steps of kneading the bulk powder, the aforementioned vehicle, a binder such as carboxymethylcellulose sodium, alginic acid or gum Arabic, and water; forming the kneaded mixture into granules if necessary; adding a lubricant such as talc or stearic acid; and then forming the mixture into tablets with a standard compression machine for forming tablets. For parenteral administration by injection, the active ingredient is dissolved along with a solubilizing agent in sterile distilled water or sterile physiological saline, and filled in ampoules. Other ingredients such as a stabilizer and a buffering agent may also be included in those formulations if necessary.

Dosage of the composition for treatment of functional or organic disorders provided by the present invention depends on various factors such as symptoms and age of the patient to be treated, route of administration, dosage form and frequency of administration, and is usually 0.1 to 1,000 mg/day/adult, preferably 1 to 500 mg/day/adult.

The present invention is further illustrated by the following examples which should not be interpreted as limiting the scope of the present invention.

Example 1. Synthesis of 1a-ethoxycarbonyl-1a, 7a-dihydro-7(1H)-cyclopropa[b]chromen-7-one To a suspension of 66 mg of sodium hydride in 6 ml of dimethylformamide in an ice bath, 363 mg of trimethylsulfoxonium iodide was added, and the mixture was stirred for 30 minutes at room temperature. Then 300 mg of 2-ethoxycarbonyl-4-oxo-4H-1-benzopyran was added, and the mixture was stirred for 15 minutes at room temperature. Ten ml of ice water was added subsequently to the reaction mixture, followed by extraction with ether. The extract was washed with a saturated sodium chloride aqueous solution, dried, filtered and then concentrated under reduced pressure to obtain a residue. The residue was purified by column chromatography on silica gel (hexane:ether=5:3), which yielded 143 mg of the above-referenced compound (yield: 45%).

Example 2. Synthesis of 1a-carboxy-1a, 7a-dihydro-7(1H)-cyclopropa [b]-chromen-7-one To a solution of 100 mg of the 1a-ethoxycarbonyl-1a, 7a-dihydro-7(1H) -cyclopropa[b]chromen-7-one synthesized in Example 1 above in 4 ml of dioxane in an ice bath, 4 ml of a 10% sodium hydroxide aqueous solution was added dropwise, and the mixture was stirred for 2 hours at room temperature. The mixture in the ice bath was then adjusted to pH 3 with concentrated hydrochloric acid, followed by extraction with ether. The extract was dried, filtered and concentrated under reduced pressure to obtain crude crystals. Recrystallization thereof from ether/hexane yielded 80 mg of the above-referenced compound (yield: 90%).

Example 3. Synthesis of 1a-isobutoxycarbonyl-1a, 7a-dihydro-7(1H)-cyclopropa[b]chromen-7-one This compound was prepared in the same manner as that described in Example 1 from 2-isobutoxycarbonyl-4-oxo-4H-1-benzopyran.

Example 4. Synthesis of 1a-(N-phenyl)carbamoyl-1a, 7a-dihydro-7(1H)-cyclopropa[b]chromen-7-one To a suspension of 633 mg of sodium hydroxide in 30 ml of dimethylformamide, 3.73 g of trimethylsulfoxonium iodide was added, and the mixture was stirred for 1 hour at 50° C. Then 1.5 g of 2-(N-phenyl)carbamoyl-4-oxo-4H-1-benzopyran was added and the mixture was stirred for 2 hours at the same temperature. Fifty ml of ice water was added subsequently to the reaction mixture, followed by extraction with ethyl acetate. The extract was washed with a saturated sodium chloride aqueous solution, dried, filtered, and concentrated under reduced pressure to obtain a residue. The residue was purified by column chromatography on silica gel (hexane:ether=3:2), which yielded 790 mg of the above-referenced compound (yield: 50%).

Example 5. Synthesis of 1a-(N-methyl-N-phenyl)carbamoyl-1a, 7a-dihydro-7(1H)-cyclopropa[b]chromen-7-one This compound was prepared in the same manner as that described in Example 4 from 2-(N-methyl-N-phenyl)-carbamoyl-4-oxo-4H-1-benzopyran.

Example 6. Synthesis of 1a-(N-3,4,5-trimethoxyphenyl)-carbamoyl-1a, 7a-dihydro-7(1H)-cyclopropa[b]chromen-7-one This compound was prepared in the same manner as that described in Example 4 from 2-(N-3,4,5-trimethoxyphenyl)-carbamoyl-4-oxo-4H-1-benzopyran.

Example 7. Synthesis of 1a-(N-3,4,5-trimethoxyphenyl-N-methyl)carbamoyl-1a, 7a-dihydro-7(1H)-cyclopropa[b]chromen-7-one This compound was prepared in the same manner as that described in Example 4 from 2-(N-3,4,5-trimethoxyphenyl-N-methyl)carbamoyl-4-oxo-4H-1-benzopyran.

Example 8. Synthesis of 1a-(N-4-(2-trimethylsilylethoxymethyl)phenyl-N-methyl)carbamoyl-1a, 7a-dihydro-7(1H)-cyclopropa[b]chromen-7-one This compound was prepared in the same manner as that described in Example 4 from 2-(N-4-(2-trimethylsilylethoxymethyl)phenyl-N-methyl)carbamoyl-4-oxo-4H-1-benzopyran.

Example 9. Synthesis of 1a-(N-4-methoxyphenyl-N-methyl)-carbamoyl-1a, 7a-dihydro-7(1H)-cyclopropa[b]chromen-7-one This compound was prepared in the same manner as that described in Example 4 from 2-(N-4-methoxyphenyl-N-methyl)carbamoyl-4-oxo-4H-1-benzopyran.

Example 10. Synthesis of 1a-(N-4-chlorophenyl-N-methyl)-carbamoyl-1a, 7a-dihydro-7(1H)-cyclopropa[b]chromen-7-one This compound was prepared in the same manner as that described in Example 4 from 2-(N-4-chlorophenyl-N-methyl)-carbamoyl-4-oxo-4H-1-benzopyran.

Example 11. Synthesis of 1a-(N-benzyl-N-methyl)carbamoyl-1a, 7a- dihydro-7(1H)-cyclopropa[b]chromen-7-one This compound was prepared in the same manner as that described in Example 4 from 2-(N-benzyl-N-methyl)-carbamoyl-4-oxo-4H-1-benzopyran.

Example 12. Synthesis of 1a-(N-methyl-N-(2-pyridyl))-carbamoyl-1a, 7a-dihydro-7(1H)-cyclopropa[b]chromen-7-one This compound was prepared in the same manner as that described in Example 4 from 2-(N-methyl-N-(2-pyridyl))-carbamoyl-4-oxo-4H-1-benzopyran.

Example 13. Synthesis of 1a-(N-methyl-N-(4-(N-t-butoxycarbonyl)piperidyl))carbamoyl-1a, 7a-dihydro-7(1H)-cyclopropa[b]chromen-7-one This compound was prepared in the same manner as that described in Example 4 from 2-(N-methyl-N-(4-(N-tert-butoxycarbonyl)-piperidyl))carbamoyl-4-oxo-4H-1-benzopyran.

Example 14. Synthesis of 1a-(N-ethyl-N-(2-methyl-2-propenyl))carbamoyl-1a, 7a-dihydro-7(1H)-cyploroya-[b]chromen-7-one This compound was prepared in the same manner as that described in Example 4 from 2-(N-ethyl-N-(2-methyl-2-propenyl))carbamoyl-4-oxo-4H-1-benzopyran.

Example 15. Synthesis of 1a-(N-(N,N-diethylaminopropyl))-carbamoyl-1a, 7a-dihydro-7(1H)-cyclopropa[b]chromen-7-one This compound was prepared in the same manner as that described in Example 4 from 2-(N-(N,N-diethylaminopropyl))carbamoyl-4-oxo-4H-1-benzo-pyran.

Example 16. Synthesis of 1a-(N-4-(1-(2-benzothiazolyl)-piperidyl)-N-methyl)carbamoyl-1a, 7a-dihydro-7(1H)-cyclopropa[b]chromen-7-one This compound was prepared in the same manner as that described in Example 4 from 2-(N-4-(1-(2-benzothiazolyl)-piperidyl)-N-methyl)carbamoyl-4-oxo-4H-1-benzopyran.

Example 17. Synthesis of 1a-(4-(N-(2-benzothiazolyl)-N-methyl)piperidyl)carbamoyl-1a, 7a-dihydro-7(1H)-cyclopropa[b]chromen-7-one This compound was prepared in the same manner as that described in Example 4 from 2-(4-N-(2-benzothiazolyl)-N-methyl)piperidyl)-carbamoyl-4-oxo-4H-1-benzopyran.

Example 18. Synthesis of 1a-(thiomorpholino)carbonyl-1a, 7a-dihydro- 7(1H)-cyclopropa[b]chromen-7-one This compound was prepared in the same manner as that described in Example 4 from 2-(thiomorpholino)carbonyl-4-oxo-4H-1-benzopyran.

Example 19. Synthesis of 1a-(1-bis(4-fluorophenyl)-methylpiperazinyl)-carbonyl-1a, 7a-dihydro-7(1H)-cyclopropa[b]chromen-7-one This compound was prepared in the same manner as that described in Example 4 from 2-(1-bis(4-fluorophenyl)-methylpiperazinyl)-carbonyl-4-oxo-4H-1-benzopyran.

Example 20. Synthesis of 1a-(1-(2-benzoxazolyl)-piperazinyl)carbonyl-1a, 7a-dihydro-7(1H)-cyclopropa[b]-chromen-7-one This compound was prepared in the same manner as that described in Example 4 from 2-(1-(2-benzoxazolyl)-piperazinyl)carbonyl-4-oxo-4H-1-benzo-pyran.

Example 21. Synthesis of 1a-(1-(4-fluorophenyl)-piverazinyl)carbonyl-1a, 7a-dihydro-7(1H)-cyclopropa[b]-chromen-7-one This compound was prepared in the same manner as that described in Example 4 from 2-(1-(4-fluorophenyl)-piperazinyl)carbonyl-4-oxo-4H-1-benzopyran.

Example 22. Synthesis of 1a-(1-(5-fluoro-2-pyrimidyl)-piperazinyl)carbonyl-1a, 7a-dihydro-7(1H)-cyclopropa[b]-chromen-7-one This compound was prepared in the same manner as that described in Example 4 from 2-(1-(5-fluoro-2-pyrimidyl)-piperazinyl)carbonyl-4-oxo-4H-1-benzopyran.

Example 23. Synthesis of 1a-(N-methyl-N-phenyl)carbamoyl-1a, 7a-dihydro-5-methoxy-7(1H)-cyclopropa[b]chromen-7-one This compound was prepared in the same manner as that described in Example 4 from 6-methoxy- 2-(N-methyl-N-phenyl)carbamoyl-4-oxo-4H-1-benzo-pyran.

Example 24. Synthesis of 1a-(N-methyl-N-phenyl)carbamoyl-1a, 7a-dihydro-5-methoxymethyloxy-7(1H)-cyclopropa[b]-chromen-7-one This compound was prepared in the same manner as that described in Example 4 from 6-methoxymethyloxy-2-(N-methyl-N-phenyl)carbamoyl-4-oxo-4H-1-benzopyran.

Example 25. Synthesis of 1a-(N-methyl-N-phenyl)carbamoyl-1a, 7a-dihydro-5-hydroxy-7(1H)-cyclopropa[b]chromen-7-one To 15 ml of a solution of 500 mg of 1a-(N-methyl-N-phenyl)carbamoyl-1a, 7a-dihydro-5-methoxymethyloxy-7(1H)-cyclopropa[b]chromen-7-one (compound prepared in Example 24) in 50% acetic acid, two drops of concentrated hydrochloric acid were added and stirred for 30 minutes at 80° C. Ten ml of ice water was added to the reaction mixture, followed by extraction with ethyl acetate. The resultant extract was dried, then filtered and concentrated under reduced pressure to obtain a residue. The residue was purified by column chromatography on silica gel (hexane: ethyl acetae=3:2), which yielded 333 mg of the above-referenced compound (yield: 76%).

Example 26. Synthesis of 5-allyloxy-1a-(bis(4-fluorophenyl) methyl piperazinyl)carbamoyl-1a, 7a-dihydro- 7(1H)-cyclopropa[b]chromen-7-one This compound was prepared in the same manner as that in Example 4 from 6-allyloxy-2-(bis(4-fluorophenyl) methyl-piperazinyl)carbamoyl-4-oxo-4H-1-benzopyran.

Example 27. Synthesis of 5-allyloxy-1a-(4-(N-(2-benzothiazolyl)-N-ethyl)piperidyl)-carbamoyl-1a, 7a-dihydro-7(1H)-cyclopropa[b]chromen-7-one This compound was prepared in the same manner as that in Example 4 from 6-allyloxy-2-(4-(N-(2-benzothiazolyl)-N-methyl)piperidyl) carbamoyl-4-oxo-4H-1-benzopyran.

Example 28. Synthesis of 1a-(4-(N-(2-benzothiazolyl)-N-methyl) piperidyl)carbamoyl-1a, 7a-dihydro-5-hydroxy-7(1H)7-cyclopropa[b]chromen-7-one Ten ml of a solution of 315 mg of 5-allyloxy-1a-(4-(N-(2-benzothia-zolyl)-N-methyl)piperidyl)carbamoyl-1a, 7a-dihydro-7(1H)-cyclopropa[b]chromen-7-one (compound prepared in Example 27), 303 mg of 1,4-diaza-bicyclo-[2, 2,2]octane (DABCO) and 155 mg of rhodium triphenylphosphine chloride complex in 90% ethanol was heated with stirring at 80° C. for 5 hours. Fifteen ml of ice cold water was then added to the reaction mixture, followed by extraction with ether. The extract was washed with 5% HCl (10 ml×2), dried, filtered and concentrated under reduced pressure to obtain a residue. The residue was purified by column chromatography on silica gel (hexane:ethyl acetae= 3:2), which yielded 188 mg of the above-referenced compound (yield: 65%).

Example 29. Synthesis of 1a-(N-methyl-N-phenyl) carbamoyl-1a, 7a-dihydro-6-hydroxy-7(1H)-cyclopropa[b] chromen-7-one 5-Methoxymethyloxy-2-(N-methyl-N-phenyl) carbamoyl-4-oxo-4H-1-benzopyran was cyclopropanated in the same manner as that described in Example 4 and subsequently processed as in Example 25 to obtain the above compound.

Example 30. Synthesis of 1a-(bis(4-fluorophenyl)methyl-piperazinyl)car-bamoyl-1a, 7a-dihydro-6-hydroxy-7(1H)-cyclopropa[b]chromen-7-one 2-(Bis(4-fluorophenyl)methylpiperazinyl)carbamoyl-5-methoxymethyl-oxy-4-oxo-4H-1-benzopyran was cyclopropanated as described in Example 4 and then treated in the same manner as in Example 25 to obtain the above compound.

Example 31. Synthesis of 1a-(4-(N-(2-benzothiazolyl)-N-methyl)piperidyl)carbamoyl-1a, 7a-dihydro-6-hydroxy-7 (1H)-cyclopropa[b]chromen-7-one 2-(4-(N-(2-Benzothiazolyl)-N-methyl)piperidyl)-carbamoyl-5-methoxy-methyloxy-4-oxo-4H-1-benzopyrazone was cyclopropanated as described in Example 4 and then treated in the same manner as in Example 25 to obtain the above compound.

Characterization of the compounds obtained in Examples 1 to 31 is presented in Table 1.

| Example No. | Structural formula | Properties | IR | $^1$H-NMR (CDCl$_3$) |
|---|---|---|---|---|
| 1 | | colorless crystal m.p. 89–90° C. (ether/hexane) | (CHCl$_3$) 3020, 1738 1674, 1608 1464, 1317 1231, 1150 | 1.35(3H, t), 1.57(1H, dd), 2.17(1H, dd), 2.79(1H, dd), 4.34(2H, q), 7.07–7.14 (2H, m), 7.53(1H, td), 7.89(1H, dd) |
| 2 | | colorless crystal m.p. 207–209° C. (decomposed) (ether/hexane) | (KBr) 3411, 3067 2930, 2702 2635, 2578 1736, 1634 1608, 1577 1468, 1332 1235, 1160 | (d$_6$-DMSO) 1.64(1H, dd), 2.10(1H, dd), 2.62(1H, dd), 7.14(2H, m), 7.62(1H, t), 7.77(1H, dd), 13.62(1H, bs) |
| 3 | | colorless crystal | (CHCl$_3$) 2962, 2876 2360, 1742 1678, 1610 1317, 1292 1242, 1151 | 0.97(6H, d), 1.59(1H, dd), 1.94–2.07(1H, m), 2.17(1H, dd), 2.80(1H, dd), 4.03(2H, d), 7.03–7.14(2H, m), 7.53(1H, td), 7.89(1H, dd) |
| 4 | | colorless crystal m.p. 150–152° C. (ether/hexane) | (CHCl$_3$) 3417, 3019 1682, 1602 1538, 1464 1315, 931 | 1.58(1H, dd), 2.32(1H, dd), 2.88(1H, dd), 7.14–7.21 (3H, m), 7.38(2H, t), 7.56–7.63(3H, m), 7.96(1H, dd), 8.48(1H, bs) |
| 5 | | colorless crystal m.p. 101–103° C. (hexane/ether) | (CHCl$_3$) 3019, 1666 1608, 1596 1496, 1464 1398, 1316 1222, 1127 | 1.27(1H, dd), 2.32(1H, dd), 2.61(1H, dd), 3.39(3H, s), 6.29(1H, bd), 6.91(1H, t), 7.00–7.07(1H, m), 7.16–7.25(5H, m), 7.72(1H, dd) |
| 6 | | colorless crystal | (CHCl$_3$) 3418, 3023 3009, 1682 1610, 1540 1509, 1463 1416, 1315 1231, 1212 | 1.59(1H, dd), 2.31(1H, dd), 2.87(1H, dd), 3.84(3H, s), 3.89(6H, s), 6.90(2H, s), 7.15–7.21(2H, m), 7.60(1H, td), 7.95–7.99(1H, m), 8.39(1H, s) |
| 7 | | colorless crystal | (CHCl$_3$) 3028, 3011 1670, 1608 1595, 1505 1464, 1217 1131 | 1.30(1H, dd), 2.40(1H, dd), 2.53(1H, dd), 3.37(3H, s), 3.48(3H, s), 3.72(6H, s), 6.39–6.46(3H, m), 6.94(1H, t), 7.23–7.33(1H, m), 7.75(1H, dd) |

-continued

| Example No. | Structural formula | Properties | IR | $^1$H-NMR (CDCl$_3$) |
|---|---|---|---|---|
| 8 | (chromanone cyclopropane carboxamide, N-(4-OSEM-phenyl), Me) | colorless crystal | (CHCl$_3$) 2962, 1670 1608, 1558 1541, 1508 1464, 1398 1316, 1262 1208, 1097 1023 | 0.004(9H, s), 0.91(2H, t), 1.26(1H, dd), 2.28(1H, dd), 2.57(1H, dd), 3.34(3H, s), 3.65(2H, t), 4.98(2H, s), 6.38(1H, bd), 6.83–6.91(3H, m), 7.11(2H, d), 7.24–7.30(1H, m), 7.74(1H, bd) |
| 9 | (chromanone cyclopropane carboxamide, N-(4-OMe-phenyl), Me) | colorless crystal | (CHCl$_3$) 3011, 2360 1670, 1608 1512, 1464 1316, 1249 1213 | 1.25(1H, dd), 2.29(1H, dd), 2.56(1H, dd), 3.34(3H, s), 3.60(3H, s), 6.38(1H, dd), 6.69(2H, d), 6.91(2H, t), 7.11(2H, d), 7.72(1H, bd) |
| 10 | (chromanone cyclopropane carboxamide, N-(4-Cl-phenyl), Me) | colorless crystal | (CHCl$_3$) 2963, 1670 1608, 1540 1492, 1464 1262, 1212 | 1.30(1H, dd), 2.32(1H, dd), 2.62(1H, dd), 3.36(3H, s), 6.32(1H, bd), 6.96(1H, t), 7.12–7.21(4H, m), 7.32(1H, td), 7.77(1H, dd) |
| 11 | (chromanone cyclopropane carboxamide, N-benzyl, Me) | colorless crystal | (CHCl$_3$) 3032, 3006 2364, 1676 1607, 1464 1316, 1262 1224, 1218 1212, 1104 | 1.45–1.51(1H, m), 2.21(1H, m), 2.70(1H, m), 2.99 and 3.08(3H, each s), 3.68(1H, s), 3.72(1H, s), 6.52–6.58(1H, m), 7.00–7.12(2H, m), 7.30–7.39(4H, m), 7.48–7.55(1H, m), 7.91(1H, td) |
| 12 | (chromanone cyclopropane carboxamide, N-(2-pyridyl), Me) | colorless crystal | (CHCl$_3$) 2962, 1676 1604, 1558 1473, 1412 1262, 1096 1024 | 1.35(1H, dd), 2.44(1H, dd), 2.75(1H, dd), 3.47(3H, s), 6.26(1H, d), 6.57(1H, dd), 6.89–6.98(2H, m), 7.20(1H, d), 7.43(1H, td), 7.55(1H, dd), 8.09(1H, dd) |
| 13 | (chromanone cyclopropane carboxamide, N-(4-NBoc-piperidinyl), Me) | colorless crystal | (CHCl$_3$) 3032, 3011 2400, 1651 1505, 1261 1199 | 1.26(1H, dd), 1.46(9H, s), 1.63–1.77(3H, m), 2.17(1H, dd), 2.60(1H, dd), 2.79–2.92(2H, m), 2.98(3H, s), 3.93(1H, m), 4.20(2H, m), 4.48(1H, m), 4.48(1H, m), 6.97(1H, dd), 7.12(1H, t), 7.51(1H, td), 7.92(1H, bd) |
| 14 | (chromanone cyclopropane carboxamide, N-(2-methylallyl), Et) | colorless crystal | (CHCl$_3$) 3008, 2963 1674, 1645 1608, 1579 1464, 1316 1261, 1208 | 1.13–1.25(3H, m), 1.41–1.53(1H, m), 1.65 and 1.71(3H, s), 2.15–2.23(1H, m), 2.62(1H, dd), 3.39–3.48(2H, m), 3.91–4.05(2H, m), 4.88(2H, dd), 6.97(1H, dd), 7.10(1H, dd), 7.52(1H, dd), 7.92(1H, t) |

-continued

| Example No. | Structural formula | Properties | IR | ¹H-NMR (CDCl₃) |
|---|---|---|---|---|
| 15 | | colorless crystal | — | 1.01(6H, t), 1.47(1H, dd), 2.20(1H, dd), 2.58–2.70(7H, m), 2.77(1H, dd), 3.40–3.52(2H, m), 7.04–7.14(2H, m), 7.54(1H, td), 7.92(1H, dd) |
| 16 | | amorphous powder | (CHCl₃) 3018, 2400 1651, 1645 1605, 1537 1315, 1216 | 1.49–1.51(1H, m), 1.83–1.95(4H, m), 2.18(1H, m), 2.62(1H, m), 2.99(3H, s), 3.21–3.30(2H, m), 4.25–4.33(2H, m), 4.60–4.69(1H, m), 6.96–7.01(1H, m), 7.06–7.14(2H, m), 7.29(1H, bt), 7.52–7.55(2H, m), 7.59(1H, d), 7.91–7.96(1H, m) |
| 17 | | colorless oil | (CHCl₃) 3023, 3016 3012, 2400 1674, 1607 1535, 1463 | 1.51(1H, dd), 1.81–1.98(5H, m), 2.16(2H, m), 2.68(1H, m), 3.05(3H, s), 3.20(1H, m), 4.55(1H, m), 4.71(1H, m), 6.99–7.15(3H, m), 7.26–7.33(1H, m), 7.51–7.62(3H, m), 7.93(1H, dd) |
| 18 | | colorless crystal | (CHCl₃) 3018, 2399 1674, 1606 | 1.48(1H, dd), 2.12(1H, dd), 2.64(1H, dd), 2.71–2.72(4H, m), 3.82–4.00(4H, m), 6.99(1H, d), 7.13(1H, td), 7.54(1H, ddd), 7.93(1H, dd) |
| 19 | | yellow oil | (CHCl₃) 3020, 2816 1735, 1718 1671, 1648 1608, 1560 1508, 1464 | 1.43(1H, dd), 2.12(1H, dd), 2.34–2.41(4H, m), 2.59(1H, dd), 3.60–3.75(4H, m), 4.24(1H, s), 6.93–7.02(5H, m), 7.09(1H, td), 7.31–7.38(4H, m), 7.50(1H, ddd), 7.88(1H, dd) |
| 20 | | colorless crystal m.p. 188–191° C. (methylene chloride/ether/ hexane) | (CHCl₃) 3025, 3016 1673, 1632 1578, 1461 | 1.53(1H, dd), 2.15(1H, dd), 2.70(1H, dd), 3.77–3.87(8H, m), 6.99–7.23(5H, m), 7.39(1H, bd), 7.56(1H, ddd), 7.95(1H, dd) |
| 21 | | colorless crystal | (CHCl₃) 3007, 2825 1674, 1608 1510, 1463 1446, 1316 1233 | 1.50(1H, dd), 2.16(1H, dd), 2.66(1H, dd), 3.15(4H, t), 3.83(4H, t), 6.85–6.92(2H, m), 6.94–7.02(3H, m), 7.10–7.16(1H, m), 7.51–7.57(1H, m), 7.94(1H, dd) |

-continued

| Example No. | Structural formula | Properties | IR | $^1$H-NMR (CDCl$_3$) |
|---|---|---|---|---|
| 22 | | amorphous powder | (CHCl$_3$) 3676, 3024 3018, 2862 2366, 1675 1608, 1560 1496, 1443 1216 | 1.51(1H, dd), 2.15(1H, dd), 2.68(1H, dd), 3.73–3.80(4H, m), 3.85–3.88(4H, m), 7.00(1H, bd), 7.13(1H, dd), 7.54(1H, ddd), 7.94(1H, dd), 8.22(2H, s) |
| 23 | | amorphous powder | (CHCl$_3$) 3019, 1662 1619, 1596 1486, 1465 1434, 1397 1347, 1292 1222, 1212 1178, 1127 | 1.22(1H, dd), 2.29(1H, dd), 2.60(1H, dd), 3.38(3H, s), 3.73(3H, s), 6.24(1H, dt), 6.86(1H, dd), 7.06(1H, tt), 7.13(1H, d), 7.16–7.24(4H, m) |
| 24 | | amorphous powder | (CHCl$_3$) 2936, 2383 1666, 1597 1485, 1436 1397, 1349 1292, 1154 1120, 1090 1002 | 1.24(1H, dd), 2.28(1H, dd), 2.61(1H, dd), 3.38(2H, s), 3.43(3H, s), 5.06(2H, dd), 6.25(1H, m), 6.96(1H, dd), 7.07(1H, m), 7.18–7.25(3H, m), 7.32(2H, d) |
| 25 | | amorphous powder | (CHCl$_3$) 3307, 2992 1726, 1666 1596, 1496 1456, 1399 1378, 1347 1319, 1273 1169, 1124 | 1.24(1H, dd), 2.28(1H, dd), 2.58(1H, dd), 3.37(3H, s), 5.30(1H, bs), 6.23(1H, m), 6.82(1H, dd), 6.97–7.12(2H, m), 7.18–7.24(3H, m), 7.36–7.39(1H, m) |
| 26 | | oily substance | (CHCl$_3$) 3028, 3012 2816, 2400 1732, 1652 1506, 1483 1439, 1296 1230, 1203 1176 | 1.38(1H, dd), 2.08(1H, dd), 2.40(4H, m), 2.56(1H, dd), 3.64(4H, m), 4.24(1H, s), 4.51(2H, d), 5.28(1H, d), 5.39(1H, d), 5.98–6.05(1H, m), 6.87(1H, d), 6.95–6.99(4H, m), 7.12(1H, dd), 7.29–7.35(5H, m) |
| 27 | | oily substance | (CHCl$_3$) 3030, 2400 1674, 1538 1484, 1230 1198 | 1.45(1H, dd), 1.79–1.85(2H, m), 1.94–2.04(1H, m), 2.12(1H, m), 2.64(1H, m), 3.01(1H, m), 3.05(3H, s), 3.21(1H, m), 4.51(2H, m), 4.54(2H, bs), 4.71(1H, m), 5.29(1H, d), 5.40(1H, d), 6.01–6.07(1H, m), 6.93(1H, dd), 7.05–7.09(1H, m), 7.16(1H, dd), 7.27–7.34(2H, m), 7.54(1H, dd), 7.59(1H, dd), 8.02(1H, bs) |

| Ex-ample No. | Structural formula | Properties | IR | $^1$H-NMR (CDCl$_3$) |
|---|---|---|---|---|
| 28 | | amorphous powder | (CHCl$_3$) 3019, 1652 1537, 1456 1424, 1317 1288, 1266 1222, 1208 1168, 1126 1064, 1014 | 1.45(1H, dd), 1.82–1.84(2H, m), 1.96(2H, m), 2.65(1H, m), 3.05(3H, s), 3.24(1H, m), 3.49(1H, m), 4.54(2H, m), 4.70(1H, m), 6.91(1H, d), 7.05–7.09(2H, m), 7.28–7.31(2H, m), 7.54(1H, d), 7.60(1H, d) |
| 29 | | oily substance | (CHCl$_3$) 3436, 3017 2400, 1792 1642, 1596 1496, 1462 1404, 1264 1224, 1218 1160, 1055 | 1.24(1H, dd), 2.34(1H, dd), 2.55(1H, dd), 3.38(3H, s), 5.71–5.75(1H, m), 6.38(1H, d), 7.08–7.25(6H, m), 11.62(1H, s) |
| 30 | | colorless crystal 197–199° C. (methanol ether) | (KBr) 3446, 2920 2360, 1667 1646, 1579 1512, 1461 1435, 1391 1263, 1232 1185, 1164 | 1.40(1H, dd), 2.13(1H, dd), 2.42(4H, t), 2.54(1H, dd), 3.68(4H, t), 4.25(1H, s), 6.38(1H, d), 6.54(1H, d), 6.94–7.03(4H, m), 7.32–7.38(5H, m), 11.71(1H, s) |
| 31 | | oily substance | (CHCl$_3$) 3022, 3016 2400, 1645 1538, 1224 1220, 1210 1208, 1043 930, 850 | 1.47(1H, dd), 1.76–1.86(2H, m), 1.95–2.02(2H, m), 2.16(1H, m), 2.63(1H, m), 2.88(1H, m), 3.05(3H, s), 3.28(1H, m), 4.45(1H, m), 4.55(1H, m), 4.69(1H, m), 6.44(1H, d), 6.58(1H, d), 7.07(1H, t), 7.30(1H, t), 7.38(1H, t), 7.57(2H, dd), 11.74(1H, s) |

Example 32. Synthesis of 1a-ethoxycarbonyl-1a, 7a-dihydro-7(1H)-hydro-xyiminocyclopropa [b]chromen Eight ml of a solution of 380 mg of 1a-ethoxycarbonyl-1a, 7a-dihydro-7(1H)-cyclopropa[b]chromen-7-one (compound prepared in Example 1) and 137 mg of hydroxyamine hydrochloride in 8 ml of pyridine was stirred for 2 hours at 100° C. Ten ml of ice water was then added to the reaction mixture, followed by extraction with ethyl acetate. The resultant extract was washed with a saturated sodium chloride aqueous solution, dried, filtered and concentrated under reduced pressure to obtain crude crystals. Recrystallization of the crystals from ether/hexane yielded 275 mg of the above-referenced compound (yield: 8%).

Example 33. Synthesis of 1a-carboxy-1a, 7a-dihydro-7(1H)-hydroxyimino-cyclopropa [b]chromen This compound was prepared in the same manner as in Example 2 from 1a-ethoxycarbonyl-1a, 7a-dihydro-7(1H)-hydroxyiminocyclopropa[b]chromen-7-one (compound in Example 32).

Example 34. Synthesis of 1a-isobutoxy-1a, 7a-dihydro-7(1H)-hydroxy-iminocyclopropa[b]chromen This compound was prepared in the same manner as described in Example 32 from 1a-isobutoxy-1a, 7a-dihydro-7(1H)-hydroxyimino-cyclopropa[b]chromen-7-one (compound in Example 3).

Example 35. Synthesis of 1a-(N-phenyl)carbamoyl-1a, 7a-dihydro-7(1H)-hydroxyiminocyclopropa[b]chromen This compound was prepared in the same manner as described in Example 32 from 1a-(N-phenyl)carbamoyl-1a, 7a-dihydro-7(1H)-cyclopropa[b]chromen-7-one (compound in Example 4).

Example 36. Synthesis of 1a-(N-methyl-N-phenyl) carbamoyl-1a, 7a-dihydro-7(1H)-hydroxyiminocyclopropa [b]chromen This compound was prepared in the same manner as described in Example 32 from 1a-(N-methyl-N-phenyl)-carbamoyl-1a, 7a-dihydro-7(1H)-cyclopropa[b]chromen-7-one (compound in Example 5).

Example 37. Synthesis of 1a-(N-3,4,5-trimethoxyphenyl)-carbamoyl-1a, 7a-dihydro-7(1H)-hydroxyiminocyclopropa [b]chromen This compound was prepared in the same manner as described in Example 32 from 1a-(N-3,4,5-trimethoxyphenyl)carbamoyl-1a, 7a-dihydro-7(1H)-cyclopropa[b]chromen-7-one (compound in Example 6).

Example 38. Synthesis of 1a-(N-3.4.5-trimethoxyphenyl-N-methyl)carbamoyl-1a, 7a-dihydro-7(1H)-hydroxyiminocyclopropa[b]chromen This compound was prepared in the same manner as described in Example 32 from 1a-(N-3,4,5-trimethoxyphenyl-N-methyl)carbamoyl-1a, 7a-dihydro-7(1H)-cyclopropa[b]chromen-7-one (compound in Example 7).

Example 39. Synthesis of 1a-(N-4-(2-trimethylsilylethoxymethyl)phenyl-N-methyl)carbamoyl-1a, 7a-dihydro-7(1H)-hydroxyiminocyclopropa[b]chromen This compound was prepared in the same manner as in Example 32 from 1a-(N-4-(2-trimethylsilylethoxymethyl)-phenyl-N-methyl)carbamoyl- 1a, 7a-dihydro-7(1H)-cyclopropa-[b]-chromen-7-one.

Example 40. Synthesis of 1a-(N-4-hydroxyphenyl-N-methyl)carbamoyl-1a, 7a-dihydro-7(1H)-hydroxyiminocyclopropa[b]chromen Eight ml of trifluoroacetic acid was added dropwise to 10 ml of a solution of 1a-(N-4-(2-trimethylsilylethoxy-methyl)phenyl-N-methyl)carbamoyl-1a, 7a-dihydro-7(1H)-cyclopropa[b]-chromen-7-one (compound in Example 39) in methylene chloride in an ice bath. After stirring for 30 minutes at room temperature, the reaction mixture was adjusted to pH 9 with a saturated sodium hydrogen carbonate solution and extracted with ethyl acetate. The extract was dried, filtered and concentrated under reduced pressure to obtain a residue. The residue was purified by column chromatography on silica gel (hexane:ethyl acetae=1:1), which yielded 219 mg (quantitative) of the above-referenced compound.

Example 41. Synthesis of 1a-(N-4-methoxyphenyl-N-methyl)carbamoyl-1a, 7a-dihydro-7(1H)-hydroxyiminocyclopropa[b]chromen This compound was prepared in the same manner as described in Example 32 from 1a-(N-4-methoxyphenyl-N-methyl)carbamoyl-1a, 7a-dihydro-7(1H)-cyclopropa[b]chromen-7-one (compound in Example 9).

Example 42. Synthesis of 1a-(N-4-chlorophenyl-N-methyl)-carbamoyl-1a, 7a-dihydro-7(1H)-hydroxyiminocyclopropa-[b]chromen This compound was prepared in the same manner as in Example 32 from 1a-(N-4-chlorophenyl-N-methyl)carbamoyl-1a, 7a-dihydro-7(1H)-cyclopropa[b]chromen-7-one (compound in Example 10).

Example 43. Synthesis of 1a-(N-benzyl-N-methyl)carbamoyl-1a, 7a-dihydro-7(1H)-hydroxyiminocyclopropa[b]chromen This compound was prepared in the same manner as in Example 32 from 1a-(N-benzyl-N-methyl)carbamoyl-1a, 7a-dihydro-7(1H)-cyclo-propa[b]chromen-7-one (compound in Example 11).

Example 44. Synthesis of 1a-(N-methyl-N-(2-pyridyl))-carbamoyl-1a, 7a-dihydro-7(1H)-hydroxyiminocyclopropa-[b]chromen This compound was prepared in the same manner as in Example 32 from 1a-(N-methyl-N-(2-pyridyl))carbamoyl-1a, 7a-dihydro-7(1H)-cyclo-propa[b]chromen-7-one (compound in Example 12).

Example 45. Synthesis of 1a-(N-methyl-N-(4-(N-tert-butoxycarbonyl)piperidyl))carbamoyl-1a, 7a-dihydro-7(1H)-hydroxyiminocyclopropa[b]chromen This compound was prepared in the same manner as in Example 40 after conversion into an oxime compound by the same method as that in Example 32 from 1a-(N-methyl-N-(4-(N-tert-butoxycarbonyl)-piperidyl))carbamoyl-1a, 7a-dihydro-7(1H)-cyclopropa-[b]chromen-7-one (compound in Example 13).

Example 46. Synthesis of 1a-(N-ethyl-N-(2-methyl-2-propenyl))carbamoyl-1a, 7a-dihydro-7(1H)-hydroxyiminocyclopropa[b]chromen This compound was prepared in the same manner as in Example 32 from 1a-(N-ethyl-N-(2-methyl-2-propenyl))-carbamoyl-1a, 7a-dihydro-7(1H)-cyclopropa[b]chromen-7-one (compound in Example 14).

Example 47. Synthesis of 1a-(N-(N,N-diethylaminopropyl))-carbamoyl-1a, 7a-dihydro-7(1H)-hydroxyiminocyclopropa-[b]chromen This compound was prepared in the same manner as in Example 32 from 1a-(N-(N,N-diethylaminopropyl))carbamoyl-1a, 7a-dihydro-7(1H)-cyclopropa[b]chromen-7-one (compound in Example 15).

Example 48. Synthesis of 1a-(N-4-(1-(2-benzothiazolyl)-piperidyl)-N-methyl)carbamoyl-1a, 7a-dihydro-7(1H)-hydroxyiminocyclopropa[b]chromen This compound was prepared in the same manner as in Example 32 from 1a-(N-4-(1-(2-benzothiazolyl)piperidyl)-N-methyl)carbamoyl-1a, 7a-dihydro-7(1H)-cyclopropa[b]chromen-7-one (compound in Example 16).

Example 49. Synthesis of 1a-(4-(N-(2-benzothiazolyl)-N-methyl) piperidyl) carbamoyl-1a, 7a-dihydro-7(1H)-hydroxyiminocyclopropa[b]chromen This compound was prepared in the same manner as in Example 32 from 1a-(4-(N-(2-benzothiazolyl)-N-methyl)piperidyl)-carbamoyl-1a, 7a-dihydro-7(1H)-cyclopropa[b]chromen-7-one (compound in Example 17).

Example 50. Synthesis of 1a-(thiomorpholino)carbonyl-1a, 7a-dihydro-7(1H)-hydroxyiminocyclopropa[b]chromen This compound was prepared in the same manner as in Example 32 from 1a-(thiomorpholino)carbonyl-1a, 7a-dihydro-7(1H)-cyclopropa[b]chromen-7-one (compound in Example 18).

Example 51. Synthesis of 1a-(1-bis(4-fluorophenyl)methyl-piperazinyl)carbonyl-1a, 7a-dihydro-7(1H)-hydroxyiminocyclopropa[b]chromen This compound was prepared in the same manner as in Example 32 from 1a-(1-bis(4-fluorophenyl)methyl-piperazinyl)carbonyl-1a, 7a-dihydro-7(1H)-cyclopropa[b]-chromen-7-one (compound in Example 19).

Example 52. Synthesis of 1a-(1-(2-benzoxazolyl)-piperazinyl)carbonyl-1a, 7a-dihydro-7(1H)-hydroxyiminocyclopropa[b]chromen This compound was prepared in the same manner as in Example 32 from 1a-(1-(2-benzoxazolyl)piperazinyl)-carbonyl-1a, 7a-dihydro-7(1H)cyclopropa[b]chromen-7-one (compound in Example 20).

Example 53. Synthesis of 1a-(1-(4-fluorophenyl)-piperazinyl)arbonyl-1a, 7a-dihydro-7(1H)-hydroxyiminocyclopropa[b]chromen This compound was prepared in the same manner as in Example 32 from 1a-(1-(4-fluorophenyl)piperazinyl)-carbonyl-1a, 7a-dihydro- 7(1H)-cyclopropa[b]chromen-7-one (compound in Example 21).

Example 54. Synthesis of 1a-(1-(5-fluoro-2-pyrimidinyl)-iperazinyl)carbonyl-1a, 7a-dihydro-7(1H)-hydroxyiminocyclopropa[b]chromen This compound was prepared in the same manner as in Example 32 from 1a-(1-(5-fluoro-2-pyrimidyl)piperazinyl)-carbonyl-1a, 7a-dihydro-7(1H)-cyclopropa[b]chromen-7-one (compound in Example 22).

Example 55. Synthesis of 1a-(N-methyl-N-phenyl) carbamoyl-1a, 7a-dihydro-7(1H)-methoxyiminocyclopropa[b]chromen This compound was prepared in the same manner as in Example 32 from 1a-(N-methyl-N-phenyl)carbamoyl-1a, 7a-dihydro-7(1H)cyclopropa[b]chromen-7-one (compound in Example 5) and O-methylhydroxylamine hydrochloride.

Example 56. Synthesis of 1a-(N-phenyl)carbamoyl-1a, 7a-dihydro-7(1H)-3-methylaminopropyloxyiminocyclopropa-[b]chromen To 5 ml of a solution of 308 mg of 1a-(N-phenyl)-carbamoyl-1a, 7a-dihydro-7(1H)-hydroxyiminocyclo-propa[b]chromen-7-one in dimethylformamide in an ice bath, 100 mg of sodium hydroxide was added and the mixture was stirred for 1 hour at room temperature. To this reaction mixture, 173 mg of 3-methylaminopropyl chloride hydrochloride was added and stirred for 2 hours at the same temperature. After the addition of 10 ml of ice water, the reaction mixture was extracted with ether. The extract was dried, filtered and concentrated under reduced pressure. The residue thus obtained was purified by column chromatography on silica gel (methylene chlorid:methanol=15:1) to yield a 340 mg (90%) of the above referenced compound. Furthermore, a maleic acid salt of this compound was obtained by the conventional method.

Example 57. Synthesis of 1a-(N-methyl-N-phenyl)carbamoyl- 1a, 7a-dihydro-7(1H)-3-methylamionopropyloxyimino-cyclopropa[b]chromen The above-referenced compound was prepared in the same manner as in Example 56 from 1a-(N-methyl-N-phenyl)carbamoyl-1a, 7a-dihydro-7(1H)-hydroxyiminocyclopropa[b]chromen-7-one (compound in Example 36).

Example 58. Synthesis of 1a-(N-phenyl)carbamoyl-1a, 7a-dihydro-7(1H)-3-dimethylamionopropyloxyiminocyclopropa-[b]chromen The above-referenced compound was prepared in the same manner as in Example 56 from 1a-(N-phenyl)carbamoyl-1a, 7a-dihydro-7(1H)-hydroxyiminocyclo-propa[b]chromen-7-one (compound in Example 35) and 3-dimethylamino-propylchloride hydrochloride.

Example 59. Synthesis of 1a-(N-methyl-N-phenyl)carbamoyl-1a, 7a-dihydro-7(1H)-3-dimethylaminopropyloxyimino-cyclopropa[b]chromen The above-referenced compound was prepared in the same manner as in Example 56 from 1a-(N-methyl-N-phenyl)carbamoyl-1a, 7a-dihydro-7(1H)-hydroxyiminocyclopropa[b]chromen-7-one (compound in Example 36) and 3-dimethylaminopropylchloride hydrochloride.

Example 60. Synthesis of 1a-(N-methyl-N-phenyl)carbamoyl-1a, 7a-dihydro-7(1H)-hydroxyimino-5-methoxycyclopropa-[b]chromen This compound was prepared in the same manner as in Example 32 from 1a-(N-methyl-N-phenyl)carbamoyl-1a, 7a-dihydro-5-methoxy-7(1H)-cyclopropa[b]chromen-7-one (compound in Example 23).

Example 61. Synthesis of 1a-(N-methyl-N-phenyl)carbamoyl-1a, 7a-dihydro-7(1H)-hydroxyimino-5-(methoxymethyloxy)-cyclopropa[b]chromen This compound was prepared in the same manner as in Example 32 from 1a-(N-methyl-N-phenyl)carbamoyl-1a, 7a-dihydro-5-methoxymethyl-oxy-7(1H)-cyclopropa[b]chromen-7-one (compound in Example 24).

Example 62. Synthesis of 1a-(N-methyl-N-phenyl)carbamoyl-1a, 7a-dihydro-7(1H)-hydroxyimino-5-hydroxycvclopropa-[b]chromen This compound was prepared in the same manner as in Example 40 from 1a-(N-methyl-N-phenyl)carbamoyl-1a, 7a-dihydro-7(1H)-hydroxyimino-5-(methoxymethyloxy)cyclopropa-[b]chromen-7-one (compound in Example 61).

Example 63. Synthesis of 5-allyloxy-1a-(bis(4-fluorophenyl)methyl-piperazinyl)carbamoyl-1a, 7a-dihydro-7(1H)-hydroxyiminocyclopropa[b]chromen This compound was prepared in the same manner as in Example 32 from 5-allyloxy-1a-(bis(4-fluorophenyl)-methyl-piperazinyl)carbamoyl-1a, 7a-dihydro-7(1H)-cyclopropa[b]-chromen-7-one (compound in Example 26).

Example 64. Synthesis of 5-allyloxy-1a-(4-(N-(2-benzothiazolyl)-N-methyl)piperidyl)carbamoyl-1a, 7a-dihydro-7(1H)-hydroxyiminocyclopropa[b]-chromen This compound was prepared in the same manner as in Example 32 from 5-allyloxy-1a-(4-(N-(2-benzothiazolyl)-N-methyl)piperidinyl) carbamoyl-1a, 7a-dihydro-7( 1H)-cyclopropa[b]chromen (compound in Example 27).

Example 65. Synthesis of 1a-(4-(N-(2-benzothiazolyl)-N-methyl) piperidyl)carbamoyl-1a, 7a-dihydro-5-hydroxy-7(1H)-hydroxyiminocyclopropa[b]-chromen This compound was prepared in the same manner as in Example 32 from 1a-(4-(N-(2-benzothiazolyl)-N-methyl)-piperidyl)carbamoyl-1a, 7a-dihydro-5-hydroxy-7(1H)-cyclopropa[b]chromen-7-one (compound in Example 28).

Example 66. Synthesis of 1a-(N-methyl-N-phenyl)carbamoyl-1a, 7a-dihydro-7(1H)-hydroxyimino-6-hydroxycyclopropa-[b]chromen This compound was prepared in the same manner as in Example 32 from 1a-(N-methyl-N-phenyl)carbamoyl-1a, 7a-dihydro-6-hydroxy-7(1H)-cyclopropa[b]chromen-7-one (compound in Example 29).

Example 67. Synthesis of 1a-(bis(4-fluorophenyl)methyl-piperazinyl)carbamoyl-1a, 7a-dihydro-6-hydroxy-7(1H)-hydroxyiminocyclopropa[b]chromen This compound was prepared in the same manner as in Example 32 from 1a-(bis(4-fluorophenyl)methyl-piperazinyl)carbamoyl-1a, 7a-dihydro-6-hydroxy-7(1H)-cyclopropa[b]-chromen-7-one (compound in Example 30).

Example 68. Synthesis of 1a-(4-(N-(2-benzothiazolyl)-N-methyl) piperidyl)carbamoyl-1a, 7a-dihydro-6-hydroxy-7(1H)-hydroxyiminocyclopropa[b]chromen This compound was prepared in the same manner as in Example 32 from 1a-(4-(N-(2-benzothiazolyl)-N-methyl)-piperidyl)carbamoyl-1a, 7a-dihydro-6-hydroxy-7(1H)-cyclopropa[b]-chromen-7-one (compound in Example 31).

Characterization of the compounds obtained in Examples 32 to 68 is presented in Table 2.

| Example No. | Structural formula | Properties | IR | ¹H-NMR (CDCl₃) |
|---|---|---|---|---|
| 32 | [structure: NOH, chromane with cyclopropane-COOEt] | colorless crystal m.p. 141–142° C. (ethyl acetate/hexane) | (CHCl₃) 3595, 3325 1732, 1632 1458, 1309 1154, 1070 | 1.35(6H, t), 1.48(1H, dd), 2.05(1H, dd), 3.38(1H, dd), 4.28(2H, q), 6.99(2H, dd), 7.32(1H, td), 7.51(1H, s), 7.74(1H, dd) |
| 33 | [structure: NOH, chromane with cyclopropane-COOH] | colorless crystal m.p. 186–188° C. (ether/hexane) | (KBr) 3508, 2856 1710, 1633 1607, 1575 1454, 1312 1240, 1066 964 | (d₆-DMSO) 1.41(1H, dd), 1.90(1H, dd), 3.09(1H, dd), 6.96–7.04(2H, m), 7.33(1H, td), 7.70(1H, dd), 11.43(1H, s), 13.50(1H, bs) |
| 34 | [structure: NOH, chromane with cyclopropane-COO-isobutyl] | colorless crystal m.p. 86–88° C. (ether/hexane) | (CHCl₃) 3020, 3013 2399, 1732 | 0.96(3H, s), 0.99(3H, s), 1.48(1H, dd), 2.00–2.08(2H, m), 3.38(1H, dd), 4.03(1H, dd), 6.96–7.05(2H, m), 7.32(1H, ddd), 7.63(1H, bs), 7.74(1H, dd) |
| 35 | [structure: NOH, chromane with cyclopropane-C(O)NH-Ph] | colorless crystal m.p. 193–194° C. (ether/hexane) | (CHCl₃) 3416, 3030 3012, 2399 1732, 1694 1600, 1538 1446, 1233 1200 | 1.46(1H, dd), 2.18(1H, dd), 3.48(1H, dd), 7.03–7.09(2H, m), 7.13–7.19(2H, m), 7.33–7.41(3H, m), 7.54(1H, bs), 7.61(2H, dd), 7.81(1H, dd), 8.50(1H, dd) |
| 36 | [structure: NOH, chromane with cyclopropane-C(O)N(Me)-Ph] | colorless crystal m.p. 170–171° C. (ether/hexane) | (CHCl₃) 3579, 3308 3018, 1652 1596, 1496 1456, 1398 1307, 1123 912 | 1.15(1H, dd), 2.23(1H, dd), 3.22(1H, dd), 3.37(3H, s), 6.17(1H, bd), 6.80(1H, td), 7.00–7.08(2H, m), 7.15–7.20(4H, m), 7.57–7.64(2H, m) |

-continued

| Example No. | Structural formula | Properties | IR | $^1$H-NMR (CDCl$_3$) |
|---|---|---|---|---|
| 37 | NOH, H, N, O, OMe, OMe, OMe | colorless crystal m.p. 211–213° C. (methylene chloride/ether/hexane) | (CHCl$_3$) 3021, 3106 2354, 1691 1602, 1541 1520, 1456 | (d$_6$-DMSO) 1.40(1H, dd), 1.98(1H, dd), 3.12(1H, dd), 3.66(3H, s), 3.78(6H, s), 7.03(1H, dt), 7.16–7.19(3H, m), 7.38(1H, td), 7.76(1H, d), 8.24(1H, s), 9.89(1H, s) |
| 38 | NOH, Me, N, O, OMe, OMe, OMe | colorless crystal m.p. 170–172° C. (methylene chloride/ether/hexane) | (CHCl$_3$) 3022, 3016 1601, 1535 1506, 1456 | 1.14(1H, dd), 2.31(1H, dd), 3.07(1H, dd), 3.35(3H, s), 3.50(3H, s), 3.72(6H, s), 6.31–6.37(3H, m), 6.81(1H, td), 7.07(1H, td), 7.28(1H, s), 7.64(1H, dd) |
| 39 | NOH, Me, N, O, OSEM | colorless crystal | (CHCl$_3$) 3584, 3020 2956, 2364 1652, 1510 1456, 1397 1304, 1252 1224, 1216 | 0.004(9H, s), 0.93(2H, t), 1.13(1H, dd), 2.19(1H, dd), 3.13(1H, dd), 3.34(3H, s), 3.66(2H, dt), 4.99(2H, s), 6.26(1H, dd), 6.77–6.87(3H, m), 7.01–7.09(4H, m), 7.32(1H, s), 7.60(1H, dd) |
| 40 | NOH, Me, N, O, OH | colorless crystal m.p. 190–191° C. (ether) | (CHCl$_3$) 3588, 3032 3024, 2566 1719, 1652 1602, 1514 1459 | 1.13(1H, m), 2.18(1H, dd), 3.15(1H, dd), 3.32(3H, s), 4.75(1H, m), 6.31(1H, m), 6.63(2H, m), 6.82(1H, m), 7.03–7.08(3H, m), 7.60(1H, m) |

| Example No. | Structural formula | Properties | IR | $^1$H-NMR (CDCl$_3$) |
|---|---|---|---|---|
| 41 | (structure with NOH, chromene, Me, N-(4-methoxyphenyl) amide) | colorless crystal m.p. 183–184° C. (methanol/ether) | (KBr) 3322, 1628 1576, 1514 1452 | (d$_6$-DMSO) 1.01(1H, m), 1.94(1H, dd), 2.96(1H, dd), 3.23(3H, s), 3.59(3H, s), 6.28(1H, m), 6.69–6.84(3H, m), 7.06(1H, m), 7.16(2H, d), 7.58(1H, d), 11.26(1H, s) |
| 42 | (structure with NOH, chromene, Me, N-(4-chlorophenyl) amide) | colorless crystal m.p. 200–202° C. (methylene chloride/ether) | (KBr) 3221, 1821 1587, 1574 1482, 1455 | (d$_6$-DMSO) 1.07(1H, dd), 2.00(1H, dd), 3.02(1H, dd), 3.27(3H, s), 6.25(1H, m), 6.84(1H, dt), 7.08(1H, dt), 7.19–7.30(4H, m), 7.61(1H, dd), 11.30(1H, s) |
| 43 | (structure with NOH, chromene, Me, N-benzyl amide) | colorless crystal m.p. 136–138° C. (methylene chloride/ether/hexane) | (CHCl$_3$) 3576, 3024 3011, 1651 1603, 1539 1496, 1456 1406, 1308 1233, 1217 | 1.33–1.40(1H, m), 2.08(1H, dd), 3.05(3H, s), 3.20–3.28(1H, m), 4.65(2H, s), 6.87–7.01(1H, m), 7.29–7.38(5H, m), 7.42–7.55(1H, m), 7.70–7.78(1H, m) |
| 44 | (structure with NOH, chromene, Me, N-(2-pyridyl) amide) | colorless crystal m.p. 202–205° C. (methylene chloride/ether) | (KBr) 3170, 2371 1656, 1630 1595, 1575 1485, 1456 1387 | (d$_6$-DMSO) 1.15(1H, dd), 2.08(1H, dd), 3.03(1H, dd), 6.10(1H, d), 6.84(1H, t), 6.98–7.06(2H, m), 7.38(1H, d), 7.60–7.71(2H, m), 8.09(1H, d), 11.33(1H, s) |
| 45 | (structure with NOH, chromene, Me, N-(piperidin-4-yl) amide) | colorless crystal (fumaric acid salt) m.p. 178–180° C. (methanol/ether) | (KBr) (fumaric acid salt) 3441, 3018 2856, 1633 1456, 1338 | (d$_6$-DMSO) 1.30(1H, dd), 1.48–1.68(4H, m), 1.80(1H, dd), 2.21–2.30(1H, m), 2.77(3H, s), 2.88–3.02(5H, m), 3.79(1H, m), 6.86–7.04(2H, m), 7.34(1H, t), 7.77(1H, d), 11.40(1H, s) |

| Example No. | Structural formula | Properties | IR | ¹H-NMR (CDCl₃) |
|---|---|---|---|---|
| 46 | | oily substance | (CHCl₃) 3578, 3024 3020, 3013 2945, 1640 1457 | 1.12–1.16(3H, m), 1.28–1.38(1H, m), 1.57(3H, s), 2.05(1H, dd), 3.20(1H, dd), 3.37–3.49(2H, m), 4.00(2H, s), 4.90(2H, dd), 6.87(1H, dd), 6.98–7.02(1H, m), 7.29–7.34(1H, m), 7.45(1H, bs), 7.77(1H, t) |
| 47 | | colorless crystal (fumaric acid salt) m.p. 86–87° C. (ethanol/ether/hexane) | — | 1.07(6H, t), 1.33(1H, dd), 2.06(1H, dd), 2.56–2.67(7H, m), 3.33–3.50(3H, m), 6.90–7.01(2H, m), 7.24–7.32(1H, m), 7.53(1H, bs), 7.76(1H, dd) |
| 48 | | colorless crystal m.p. 188–190° C. (methylene chloride/ether/hexane) | (CHCl₃) 3578, 3382 3020, 2362 1644, 1603 1539, 1456 | 1.37(1H, m), 1.82–1.97(4H, m), 2.05(1H, dd), 2.67–2.74(1H, m), 2.88 and 2.96(3H, s), 3.15–3.27(2H, m), 4.05–4.31(2H, m), 4.56–4.70(1H, m), 6.89(1H, bt), 7.00(1H, bt), 7.30(1H, dd), 7.47(1H, bs), 7.54–7.60(2H, m), 7.79(1H, d) |
| 49 | | colorless crystal m.p. 144–146° C. (ether/hexane) | (CHCl₃) 3023, 3017 2399, 1652 1538, 1424 1218 | 1.21(1H, dd), 1.81–2.01(5H, m), 2.79–2.96(1H, m), 3.05(3H, s), 3.12–3.34(1H, m), 3.48(1H, dd), 4.45–4.56(1H, m), 4.70(1H, m), 6.89–7.10(3H, m), 7.29–7.35(2H, m), 7.58(2H, td), 7.78(1H, dd) |

| Example No. | Structural formula | Properties | IR | ¹H-NMR (CDCl₃) |
|---|---|---|---|---|
| 50 | (chromanone oxime with thiomorpholine amide) | colorless crystal m.p. 164–165° C. (ether/hexane) | (CHCl₃) 3020, 2400 1652 | 1.36(1H, dd), 2.00(1H, dd), 2.62–2.78(4H, m), 3.21(1H, dd), 3.80–4.03(4H, m), 6.90(1H, dd), 7.00(1H, bt), 7.31(1H, ddd) 7.65(1H, s), 7.77(1H, dd) |
| 51 | (chromanone oxime with bis(4-fluorophenyl)methyl piperazine amide) | colorless crystal m.p. 177–180° C. (methylene chloride/ether/hexane) | (CHCl₃) 3021, 2400 1633, 1602 | 1.30(1H, dd), 1.97(1H, dd), 2.36–2.44(4H, m), 3.16(1H, dd), 3.63–3.69(4H, m), 4.24(1H, s), 6.85(1H, bd), 6.94–7.00(5H, m), 7.25–7.29(1H, m), 7.31–7.39(5H, m) |
| 52 | (chromanone oxime with benzothiazolyl piperazine amide) | colorless crystal m.p. 231–234° C. (methylene chloride/ether/hexane) | (CHCl₃) 3586, 3024 2990, 1734 1636, 1604 1580, 1459 | 1.40(1H, dd), 2.02(1H, dd), 3.26(1H, dd), 3.77–3.84(8H, m), 6.90(1H, dd), 6.99–7.09(2H, m), 7.19(1H, td), 7.29–7.40(3H, m), (3H, m) 7.79(1H, dd) |
| 53 | (chromanone oxime with 4-fluorophenyl piperazine amide) | colorless crystal m.p. 194–197° C. (ether/hexane) | (CHCl₃) 3020, 3016 2974, 2401 1651, 1509 | 1.37(1H, dd), 2.02(1H, dd), 3.14(4H, br), 3.23(1H, dd), 3.82(4H, br), 6.85–7.04(5H, m), 7.29–7.35(1H, m), 7.68(1H, bs), 7.78(1H, dd) |
| 54 | (chromanone oxime with 5-fluoropyrimidinyl piperazine amide) | colorless crystal m.p. 173–176° C. (methylene chloride/ether/hexane) | (CHCl₃) 3021, 3016 2399, 1651 | 1.38(1H, dd), 2.02(1H, dd), 3.24(4H, dd), 3.73(4H, br), 3.85(4H, br), 6.90(1H, dd), 7.01(1H, td), 7.32(1H, td), 7.50(1H, bs), 7.79(1H, dd), 8.21(2H, s) |

| Example No. | Structural formula | Properties | IR | $^1$H-NMR (CDCl$_3$) |
|---|---|---|---|---|
| 55 | (structure: cyclopropane with N-Me phenyl amide, chromene with NOH oxime) | oily substance | (CHCl$_3$) 3023, 3000 1652, 1598 1496, 1456 | 1.12(1H, dd), 2.17(1H, dd), 3.11(1H, dd), 3.36(3H, s), 4.02(3H, s), 6.14(1H, bd), 6.79(1H, td), 6.97–7.06(2H, m), 7.14–7.23(4H, m), 7.65(1H, dd) |
| 56 | (structure: cyclopropane with NH-phenyl amide, chromene with N-O-CH$_2$CH$_2$CH$_2$-NHMe oxime) | colorless crystal (fumaric acid salt) m.p. 108–110° C. (methanol/ether/hexane) | (KBr) (fumaric acid salt) 3400, 2944 1682, 1601 1539, 1447 1320, 1234 1153, 1060 755 | 1.47(1H, dd), 1.94(2H, dt), 2.14(1H, dd), 2.45(3H, s), 2.73(2H, t), 3.36(1H, dd), 4.24–4.33(2H, m), 7.00–7.07(2H, m), 7.13–7.19(1H, m), 7.32–7.40(4H, m), 7.61(2H, bd), 7.85(1H, dd), 8.50(1H, bs) |
| 57 | (structure: cyclopropane with N-Me phenyl amide, chromene with N-O-CH$_2$CH$_2$CH$_2$-NHMe oxime) | colorless crystal (fumaric acid salt) m.p. 138–140° C. (methanol/ether/hexane) | (KBr) (fumaric acid salt) 3450, 2960 2774, 1654 1616, 1596 1497, 1456 1394, 1230 1056, 985 | 1.12(1H, dd), 1.95(2H, dt), 2.17(1H, dd), 2.47(3H, s), 2.75(2H, t), 3.11(1H, dd), 3.36(1H, td), 4.28(2H, t), 6.13(1H, bd), 6.78(1H, td), 6.96–7.06(2H, m), 7.14–7.23(5H, m), 7.64(1H, dd) |
| 58 | (structure: cyclopropane with NH-phenyl amide, chromene with N-O-CH$_2$CH$_2$CH$_2$-NMe$_2$ oxime) | colorless crystal (fumaric acid salt) m.p. 173–174° C. (methanol/ether) | (KBr) (fumaric acid salt) 3402, 3316 1688, 1600 1540, 1448 1318 | 1.44(1H, dd), 1.88–1.99(2H, m), 2.14(1H, dd), 2.25(6H, s), 2.41(2H, t), 3.37(1H, dd), 4.26(2H, dt), 7.01–7.07(2H, m), (2H, m), 7.13–7.19(1H, m), 7.31–7.40(3H, m), 7.58–7.63(2H, m), 7.84–7.88(1H, m), 8.51(1H, s) |

| Example No. | Structural formula | Properties | IR | $^1$H-NMR (CDCl$_3$) |
|---|---|---|---|---|
| 59 | (structure with NMe$_2$ group, cyclopropane, N-phenyl amide, Me) | colorless crystal (fumaric acid salt) m.p. 60° C. (ether/hexane) | (CHCl$_3$) 3434, 3038 2942, 2683 2371, 1654, 1616, 1595 | 1.12(1H, dd), 1.89–1.99(2H, m), 2.15–2.23(2H, m), 2.27(6H, s), 2.42(2H, t), 3.12(1H, dd), 4.25(2H, t), 6.13(1H, bd), 6.78(1H, td), 6.96–7.06(2H, m), 7.14–7.22(4H, m), 7.64(1H, dd), 8.02(1H, bs) |
| 60 | (structure with NOH, MeO, chromene, cyclopropane, N-phenyl amide, Me) | colorless crystal 73–75° C. (ether/hexane) | (CHCl$_3$) 3580, 3306 3009, 1648 1596, 1496 1487, 1466 1432, 1396 1290, 1210 1125, 1036 | 1.10(1H, dd), 2.19(1H, dd), 3.18(1H, dd), 3.36(3H, s), 3.70(3H, s), 6.11(1H, m), 6.63(1H, dd), 7.03–7.06(2H, m), 7.16–7.23(5H, m) |
| 61 | (structure with NOH, MeOCH$_2$O, chromene, cyclopropane, N-phenyl amide, Me) | oily substance | (CHCl$_3$) 3581, 3003 2936, 1648 1596, 1496 1485, 1451 1396, 1350 1289, 1213 1189, 1153 | 1.21(1H, dd), 2.18(1H, dd), 3.18(1H, dd), 3.36(3H, s), 3.43(3H, s), 5.04(2H, s), 6.10(1H, m), 6.74(1H, dd), 7.05–7.07(1H, m), 7.16–7.25(5H, m) |
| 62 | (structure with NOH, HO, chromene, cyclopropane, N-phenyl amide, Me) | colorless crystal 238–240° C. (methanol/ether) | (KBr) 3358, 3178 2966, 1627 1595, 1487 1460, 1401 1365, 1206 1124, 1075 992, 963 | (d$_6$-DMSO) 1.25(1H, m), 1.90(1H, dd), 2.97(1H, dd), 3.27(3H, s), 6.04(1H, m), 6.49(1H, m), 6.94(1H, m), 7.11(1H, m), 7.23–7.24(4h, m), 8.91(1H, bs), 11.14(1H, bs) |

-continued

| Example No. | Structural formula | Properties | IR | $^1$H-NMR (CDCl$_3$) |
|---|---|---|---|---|
| 63 | (structure with bis(4-fluorophenyl)methyl piperazine, chromene with NOH and allyloxy group) | colorless crystal 150–152° C. (ether/hexane) | (CHCl$_3$) 3020, 2399 1651, 1506 1484, 1445 1225, 1218 1209, 928 | 1.26(1H, dd), 1.93(1H, dd), 2.40(4H, m), 3.12(1H, dd), 3.65(4H, m), 4.24(1H, s), 4.47(2H, dd), 5.26(1H, dd), 5.38(1H, dd), 6.00(1H, m), 6.77(1H, d), 6.89(1H, dd), 6.95–6.99(4H, m), 7.20(1H, d), 7.32–7.35(5H, m) |
| 64 | (benzothiazole-piperidine-N-Me-piperidine chromene NOH allyloxy) | colorless crystal 118–120° C. (ether/hexane) | (CHCl$_3$) 3020, 2399 1651, 1532 1506, 1424 1225, 1216 1214, 1204 928, 794 | 1.33(1H, m), 1.82(2H, td), 1.92–2.01(1H, m), 2.91(1H, m), 3.05(3H, s), 3.22(1H, m), 3.47(1H, m), 4.38(1H, m), 4.46(1H, m), 4.50(2H, d), 4.73(1H, m), 5.27(1H, dd), 5.39(1H, d), 5.99–6.06(1H, m), 6.83(1H, d), 6.94(1H, dd), 7.06(1H, t), 7.31(2H, m), 7.57(2H, dd) |
| 65 | (benzothiazole-piperidine-N-Me-piperidine chromene NOH hydroxy) | amorphous powder | (CHCl$_3$) 3587, 3319 2953, 1646 1535, 1456 1424, 1288 1222, 1214 1126, 1014 | 1.32(1H, m), 1.76–1.83(2H, m), 1.94–1.97(3H, m), 2.86(1H, m), 3.03(3H, s), 3.09(1H, m), 4.12(1H, m), 4.35(2H, m), 4.52(2H, m), 4.67(1H, m), 6.77–6.86(2H, m), 7.07(1H, t), 7.21(1H, m), 7.29–7.31(2H, m), 7.57(2H, dd) |
| 66 | (N-Me-N-phenyl amide, cyclopropane, chromene NOH, hydroxy) | colorless crystal 157–159° C. (ether/hexane) | (CHCl$_3$) 3566, 3019 2930, 1652 1621, 1596 1496, 1464 1399, 1221 1210 | 1.12(1H, dd), 2.23(1H, dd), 3.18(1H, dd), 3.37(3H, s), 5.66(1H, m), 6.38(1H, d), 6.87(1H, t), 7.07(1H, td), 7.16–7.22(5H, m), 10.51(1H, s) |

-continued

| Example No. | Structural formula | Properties | IR | $^1$H-NMR (CDCl$_3$) |
|---|---|---|---|---|
| 67 | (structure: 8-hydroxy chromene with cyclopropane-C(=O)-N piperazine-N-CH(4-F-C$_6$H$_4$)$_2$, with =NOH group) | colorless crystal 187–189° C. (ether/hexane) | (CHCl$_3$) 3568, 3232 2818, 2358 1636, 1604 1506, 1464 1299, 1222 1213 | 1.28(1H, dd), 1.96(1H, dd), 2.39–2.45(4H, m), 3.15(1H, dd), 3.66–3.78(4H, m), 4.25(1H, s), 6.44(1H, dd), 6.94–7.01(4H, m), 7.12(1H, t), 7.32–7.37(5H, m), 7.43(1H, s), 10.63(1H, s) |
| 68 | (structure: 8-hydroxy chromene with cyclopropane-C(=O)-N piperidine-N(2-Me-benzothiazole), with =NOH group) | colorless crystal 232–234° C. (methylene chloride/ether/hexane) | (CHCl$_3$) 3573, 3224 3009, 2954 1636, 1534 1464, 1424 1318, 1224 1126, 1015 | 1.34(1H, m), 1.79–1.98(4H, m), 2.10(1H, m), 2.89(1H, m), 3.06(3H, s), 3.14–3.29(1H, m), 4.18(1H, m), 4.55(2H, m), 4.71(1H, d), 6.41(1H, d), 6.55(1H, d), 7.07(1H, t), 7.15(1H, t), 7.28–7.32(2H, m), 7.58(2H, dd), 8.43(1H, bs), 10.70(1H, bs) |

Evaluation Example 1. mGluR1 antagonistic effect as assessed with reference to intracellular $Ca^{2+}$ response in mGluR1 expressing CHO cells Since mGluR1 (metabotropic glutamate receptor 1) induces release of $Ca^{2+}$ from intracellular $Ca^{2+}$ storage sites via the formation of inositol-1,4,5-triphosphate in the pathway of the intracellular signaling system, it is possible to evaluate the antagonistic activity of the compounds of the invention against mGluR1 with reference to intracellular $Ca^{2+}$ response in CHO cells in which recombinant rat mGluR1 gene is transfected.

The present inventors applied this evaluation system to assess the mGluR1 antagonistic activity of the compounds provided by this invention using CHO cells in which rat mGluR1 gene is expressed [S. Nakanishi et al.: Neuron, 8, 757 (1992)]. Intracellular $Ca^{2+}$ release induced by 10 μM glutamic acid in the presence of various concentrations of the compounds of the present invention added to culture medium was measured by fluorometry with Fura −2 [H. Sugino et al.: Brain Res., 322,127 (1984)]. The antagonistic effect against the induced intracellular $Ca^{2+}$ elevation was thus assessed by comparison with the control response in the absence of the test compounds. As the result, all the compounds of the present invention exhibited an antagonistic effect against mGluR1, particularly the effect being remarkable with the compounds of Examples 32, 34, 35, 36, 41, 42, 43 and 53 showing 50% inhibitory concentrations ($IC_{50}$) of 100 μM or less (Table 3). $IC_{50}$ values found for reference drugs used, (S)-4CPG and MCPG [Y. Hayashi et al.: J. Neurosci., 14, 3370 (1994)] are also presented in Table 3.

TABLE 3

| Example No. | $IC_{50}$ (μM) |
|---|---|
| 32 | 23 |
| 34 | 20 |
| 35 | 3 |
| 36 | 10 |
| 41 | 100 |
| 42 | 100 |
| 43 | 20 |
| 53 | 100 |
| (S)-4CPG | 200 |
| MCPG | 700 |

ADVANTAGEOUS EFFECTS OF THE INVENTION

The present invention provides novel cyclopropachromen-carboxylic acid derivatives and its pharmaceutically acceptable salts having antagonistic activity against metabotropic glutamate receptors. The compounds of the present invention has antagonistic activity against metabotropic glutamate receptors and low toxicity, thereby having potential as drugs for improving symptoms associated with functional and/or organic disorders of the brain.

We claim:

1. A cyclopropachromencarboxylic acid derivative and its pharmaceutically acceptable salts represented by the following formula (I):

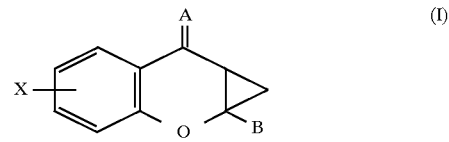

wherein A denotes a hydroxyimino group, an alkyloxyimino group having 1 to 5 carbon atoms, or the group =N—O—$(CH_2)_n$—$NR^1R^2$ where n represents an integer of 2 to 8, and each of $R^1$ and $R^2$ independently represents a hydrogen atom or alkyl group having 1 to 5 carbon atoms, respectively;

B denotes the group —$COOR^3$ where $R^3$ represents a hydrogen atom or alkyl group having 1 to 5 carbon atoms, or the group —$CONR^4R^5$ where $R^4$ and $R^5$ independently represent a hydrogen atom, alkyl group having 1 to 5 carbon atoms, alkenyl group having 2 to 5 carbon atoms, aminoalkyl group wherein N is optionally substituted, a phenyl group optionally substituted with a halogen atom or hydroxyl group in turn optionally substituted, a 2-pyridyl group, or aralkyl group having 7 to 10 carbon atoms; and X is a halogen atom or the group —$OR^6$ where $R^6$ represents a hydrogen atom an alkyl group having 1 to 5 carbon atoms, an alkenyl group having 3 to 6 carbon atoms, or an aralkyl group having 7 to 10 carbon atoms.

2. A pharmaceutical composition comprising a pharmaceutically effective amount of a cyclopropachromencarboxylic acid derivative of claim 1 or its pharmaceutically acceptable salt, together with a pharmaceutically acceptable diluent or carrier.

3. A method for treating symptoms selected from the group consisting of sequelae of cerebral infarction, sequelae of intracerebral hemorrhage, sequelae of cerebral arteriosclerosis, senile dementia, sequelae of head trauma, sequelae of surgical brain operation, Alzheimer's disease, and Parkinson's disease, which method comprises administering to a patient in need thereof an effective amount of a cyclopropachromencarboxylic acid derivative of claim 1 or its pharmaceutically acceptable salt.

4. A method of preventing the abnormal activation of metabotropic recaptor glutamate receptors which method comprises administrating to a patient in need thereof an effective amount of a cyclopropachromencarboxylic acid derivative of claim 1 or its pharmaceutically acceptable salt.

5. A method for treating a symptom arising from functional and/or organic disorders of brain, which method comprising the step of administering in need of said treatment an effective amount of a cyclopropachromencarboxylic acid derivative of claim 1 or its pharmaceutically acceptable salt.

* * * * *

UNITED STATES PATENT AND TRADEMARK OFFICE
CERTIFICATE OF CORRECTION

PATENT NO.    : 5,843,988
DATED         : December 1, 1998
INVENTOR(S)   : Annoura et al It is certified that error appears in the above-identified patent and that said letters patent is hereby corrected as shown below:

On the title page:

Item [75]  delete "Toshio Tatasuoka" insert --Toshio Tatsuoka--.

Item [30]  delete "Oct. 21, 1997 insert --Oct. 21, 1994--.

Signed and Sealed this

Thirtieth Day of March, 1999

Attest:

Q. TODD DICKINSON

Attesting Officer

Acting Commissioner of Patents and Trademarks